(12) United States Patent
Johns

(10) Patent No.: US 8,311,284 B2
(45) Date of Patent: Nov. 13, 2012

(54) INCAPACITY MONITOR

(75) Inventor: Murray Johns, Richmond (AU)

(73) Assignee: Optalert Pty Ltd, Richmond (AU)

(*) Notice: Subject to any disclaimer, the term of this patent is extended or adjusted under 35 U.S.C. 154(b) by 978 days.

(21) Appl. No.: 12/281,010

(22) PCT Filed: Feb. 28, 2007

(86) PCT No.: PCT/AU2007/000219
§ 371 (c)(1),
(2), (4) Date: Aug. 28, 2008

(87) PCT Pub. No.: WO2007/098530
PCT Pub. Date: Sep. 7, 2007

(65) Prior Publication Data
US 2009/0034796 A1    Feb. 5, 2009

(30) Foreign Application Priority Data
Mar. 1, 2006  (AU) .................. 2006901016

(51) Int. Cl.
G06K 9/00 (2006.01)
H04N 7/18 (2006.01)
G08B 23/00 (2006.01)

(52) U.S. Cl. ........ 382/104; 382/107; 382/117; 348/148; 340/575; 340/576

(58) Field of Classification Search .................. 382/104, 382/107, 117; 348/143, 148; 340/575, 576
See application file for complete search history.

(56) References Cited

U.S. PATENT DOCUMENTS

| | | | |
|---|---|---|---|
| 4,665,385 A * | 5/1987 | Henderson | 340/539.26 |
| 5,745,038 A | 4/1998 | Vance | |
| 5,845,000 A * | 12/1998 | Breed et al. | 382/100 |
| 6,070,098 A | 5/2000 | Moore-Ede et al. | |
| 6,147,612 A | 11/2000 | Ruan et al. | |
| 7,071,831 B2 | 7/2006 | Johns | |
| 7,616,125 B2 | 11/2009 | Johns | |
| 8,095,490 B2 * | 1/2012 | Nishizaki et al. | 706/46 |
| 2001/0028309 A1 | 10/2001 | Torch | |
| 2002/0180799 A1 * | 12/2002 | Peck et al. | 345/784 |
| 2003/0020755 A1 * | 1/2003 | Lemelson et al. | 345/786 |
| 2004/0044293 A1 * | 3/2004 | Burton | 600/544 |
| 2004/0233061 A1 * | 11/2004 | Johns | 340/575 |
| 2005/0007552 A1 * | 1/2005 | Fergason et al. | 351/210 |
| 2005/0020934 A1 * | 1/2005 | Potter et al. | 600/546 |
| 2008/0188777 A1 * | 8/2008 | Bedziouk et al. | 600/595 |
| 2009/0034796 A1 * | 2/2009 | Johns | 382/103 |
| 2009/0062680 A1 * | 3/2009 | Sandford | 600/544 |

(Continued)

FOREIGN PATENT DOCUMENTS
EP    0280124    8/1988
(Continued)

*Primary Examiner* — Aaron W Carter
(74) *Attorney, Agent, or Firm* — Connolly Bove Lodge & Hutz LLP

(57) ABSTRACT

A method of monitoring incapacity of a subject which includes the steps of continuously monitoring eye and eyelid movement of at least one eye of the subject; analyzing eye and eyelid movements to obtain measures of ocular quiescence and the duration of an interval of no eye or eyelid movement; and if the duration of ocular quiescence exceeds a predetermined value providing a potential incapacity warning and requesting a response within a predetermined period, and applying an emergency procedure if no response is made within a predetermined interval.

2 Claims, 3 Drawing Sheets

U.S. PATENT DOCUMENTS

2009/0141895 A1 * 6/2009 Anderson et al. ............. 380/252

FOREIGN PATENT DOCUMENTS

| WO | 9715033 A2 | 4/1997 |
| WO | 9849028 | 11/1998 |
| WO | 0024309 | 5/2000 |
| WO | 03039358 | 5/2003 |
| WO | 2005094667 | 10/2005 |
| WO | WO 2005094667 A2 * | 10/2005 |
| WO | 2006092022 | 9/2006 |

* cited by examiner

INCAPACITY MONITOR

CROSS REFERENCE TO RELATED APPLICATIONS

This application is a National Phase filing under 35 U.S.C. §371 of PCT/AU2007/000219 filed Feb. 28, 2007, which claims priority to Patent Application No. 2006901016, filed in Australia on Mar. 1, 2006. The entire contents of each of the above-applications are incorporated herein by reference.

This invention relates to monitoring inattention and particularly incapacity in vehicle drivers or machinery operators.

BACKGROUND TO THE INVENTION

The detection of drowsiness is of importance because drowsiness impairs the ability of operators of a wide range of equipment including motor vehicles, aircraft and boats as well as industrial equipment WO 03/039358 disclosed an alertness monitor that used infra red light to measure the amplitude and velocity of eyelid and eye movements to derive a measure of Drowsiness on a scale. This monitor sought to provide a real time alertness monitor that can provide a calibrated measure of the operator's alertness. There is a recent concern with the problem of driver distraction, not just drowsiness. By distraction they mean displacement of the driver's focus of visual attention from the driving task, either to a non-visual task (eg talking to other people in the vehicle, or the use of mobile phones), or to an alternative, visual task that reduces driving safety temporarily (reading a map or navigation system, adjusting a CD player or radio, etc). Thus, driver distraction is concerned with attention that is focused inappropriately, in direction and duration, for safe driving. The concept of a driver's incapacity seems to be applied primarily in the rail industry. It refers to some medical or other condition that makes the driver lose consciousness, not just enter the readily reversible states of drowsiness sleep, or distraction. This has been a major focus of interest in Australia after the a rail crash in which the driver died of a heart attack, but the train kept going and was derailed, killing passengers. The medical conditions that are most likely to be involved in such incidents are sudden death (eg heart attack or stroke), hypoglycaemia in diabetics, and epileptic seizures.

There is current system of vigilance detection in trains which involves the driver pushing a button or making some adjustment to the train controls (change speed, apply brakes etc) once every 90 secs (approx) or a siren will be sounded and the brakes applied to stop the train. However the drivers only have to be moderately alert for about 1 sec to push the button at any time during the 90-sec period. They could easily be asleep for a minute at a time, repeatedly, without this being detected by current system.

U.S. Pat. No. 6,102,870 uses eye tracker data such as fixations and saccades to infer mental states of the operator such as scanning, reading, searching, thinking and an intention to select. It is a system to enhance computer software responsiveness.

U.S. Pat. No. 6,346,887 uses a video based eye tracking system which tracks eye activity and pupil diameter and position to produce a signal representing eye activity that can be used to estimate alertness.

It is an object of this invention to provide an improved alertness monitor of the type disclosed in WO 03/039358 which can deal with incapacity.

BRIEF DESCRIPTION OF THE INVENTION

To this end the present invention provides a system for monitoring incapacity which includes
a) means to measure eye and eyelid movements
b) storage means to continuously record the measurements
c) a data processor to analyze eye and eyelid movements to obtain measures of ocular quiescence and/or duration of eye lid closure and measuring the deviation from a predetermined value for alert subjects
d) an alarm means triggered by the measurement reaching a predetermined value.

Sometimes drivers can apparently be looking straight ahead, with their eyes wide open, but they actually have their attention focused elsewhere (eg with stressful intrusive thoughts). Alternatively, in the drowsy state, they may have their eyes open but not seeing and not aware of anything. Neither of these situations would be detected by a video camera. However, the infra red detection system disclosed in WO 03/039358 can measure levels of drowsiness continuously. The optimum duration of "distraction" that should trigger a warning is of the order of 2 to 5 seconds when a vehicle is moving or a machine is in operation.

The infra red detection system disclosed in WO 03/039358 can also measure periods when there are no eye or eyelid movements. Prolonged ocular quiescence is a good marker of "incapacity". The mean duration of ocular quiescence (DOQ) per minute is the mean of the intervals between consecutive eye and eyelid movements of any kind, including saccades, blinks, vestibulo-ocular movements, etc. Relatively long periods of ocular quiescence are typical of the drowsy state for many subjects. This invention is in partly based on the analysis of the duration of such intervals for truck drivers on the road and train drivers actually driving a train. Drivers usually make some sort of eye or eyelid movement (saccades, blinks, vestibulo-ocular movements, etc) several times per sec.

Ocular quiescent periods of more than about 6 sec are rare and are used in this invention as a trigger for "potential incapacity" warning. This is preferably followed by further specific testing of the driver by asking him to push a button as soon as possible after the warning is given. This would overcome the occasional problem of false positive warnings and the brakes being applied inappropriately. Warnings caused by occasional prolonged periods of ocular quiescence that are not caused by incapacity are easily negated by the operator providing an appropriate response to the potential incapacity warning.

Each potential incapacity warning triggered by ocular quiescence requires a response from the operator. Such an action by the operator indicates that the warning was a false positive and would focus the operator's attention back on the task of driving or machine operation as the case may be.

If the operator does not respond an emergency procedure can be implemented. The emergency procedure will vary according to the type of vehicle or machine being operated and may include braking the vehicle to bring it to a stop and/or transmitting a report to a central control post.

Thus in another aspect this invention provides a method of controlling a vehicle or machine in which the operator is monitored by
a) continuously monitoring one or more of eye and eyelid movements including saccades and blinks in at least one eye of the operator
b) analyzing said eye and eyelid movements to obtain a measure of ocular quiescence and measuring the deviation from a predetermined value for alert subjects c) providing a warning when the measure deviates a predetermined amount which requires a response within a predetermined period
d) applying an emergency procedure if no response is made within the predetermined time.

Eyelid movement and saccades may be monitored using any suitable technology including video or digital camera technology to identify and measure the appropriate eye movements. However the apparatus and algortitms disclosed in WO 03/039358 are preferred.

DETAILED DESCRIPTION OF THE INVENTION

The eye monitoring apparatus used in this invention is of the same kind as described in the inventor's earlier patent application WO 03/039358. WO 03/039358 described glasses with transducers (IR-LEDs and phototransistors) on both eyes. The reason for this was that binocular coordination changed with drowsiness which made it essential to record from both eyes. However, based on further research by the inventor, it appears that the measurement of binocular coordination becomes more inaccurate as drowsiness progresses. Thus where the measurement of binocular coordination is not required recordings from one eye are sufficient for all other parameters.

It is now preferred to position two infrared emitters and at least one photo transistor detector located on the lower frame member below one eye. Dur9ing fitting of the device to an individual the emitter which provides the best signal is chosen for that individual.

Currently, video camera methods for monitoring drowsiness have both practical and theoretical problems. Some of the latter may be overcome in the future if the frame rate of cameras can be increased to about 500 Hz, which may allow velocities and AVRs to be measured. At this time infra red emission and detection is the preferred technology.

Figure 1:
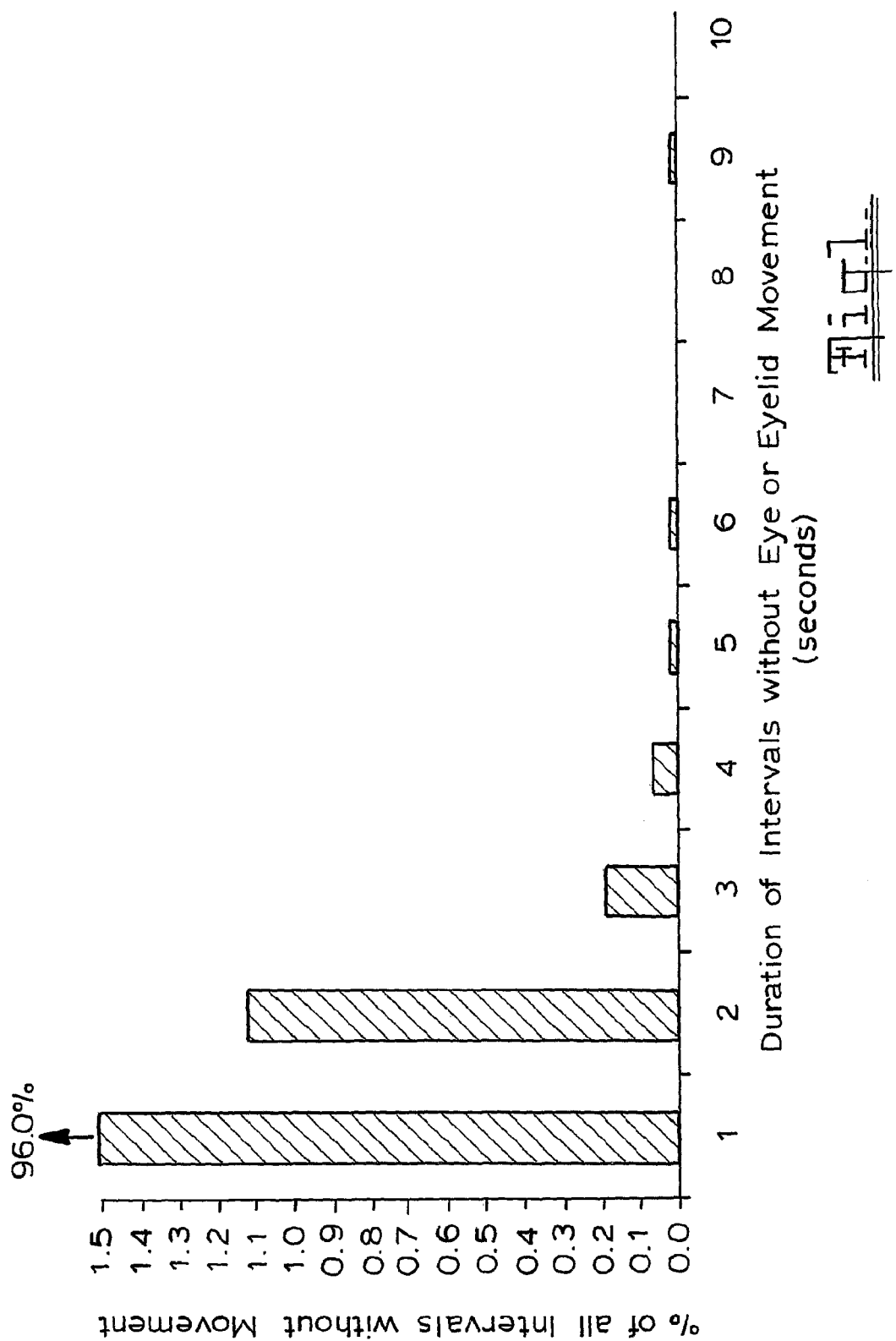
FIG. 1 is a frequency histogram illustrating the frequency of various periods of ocular quiescence in train drivers.
Figure 2:
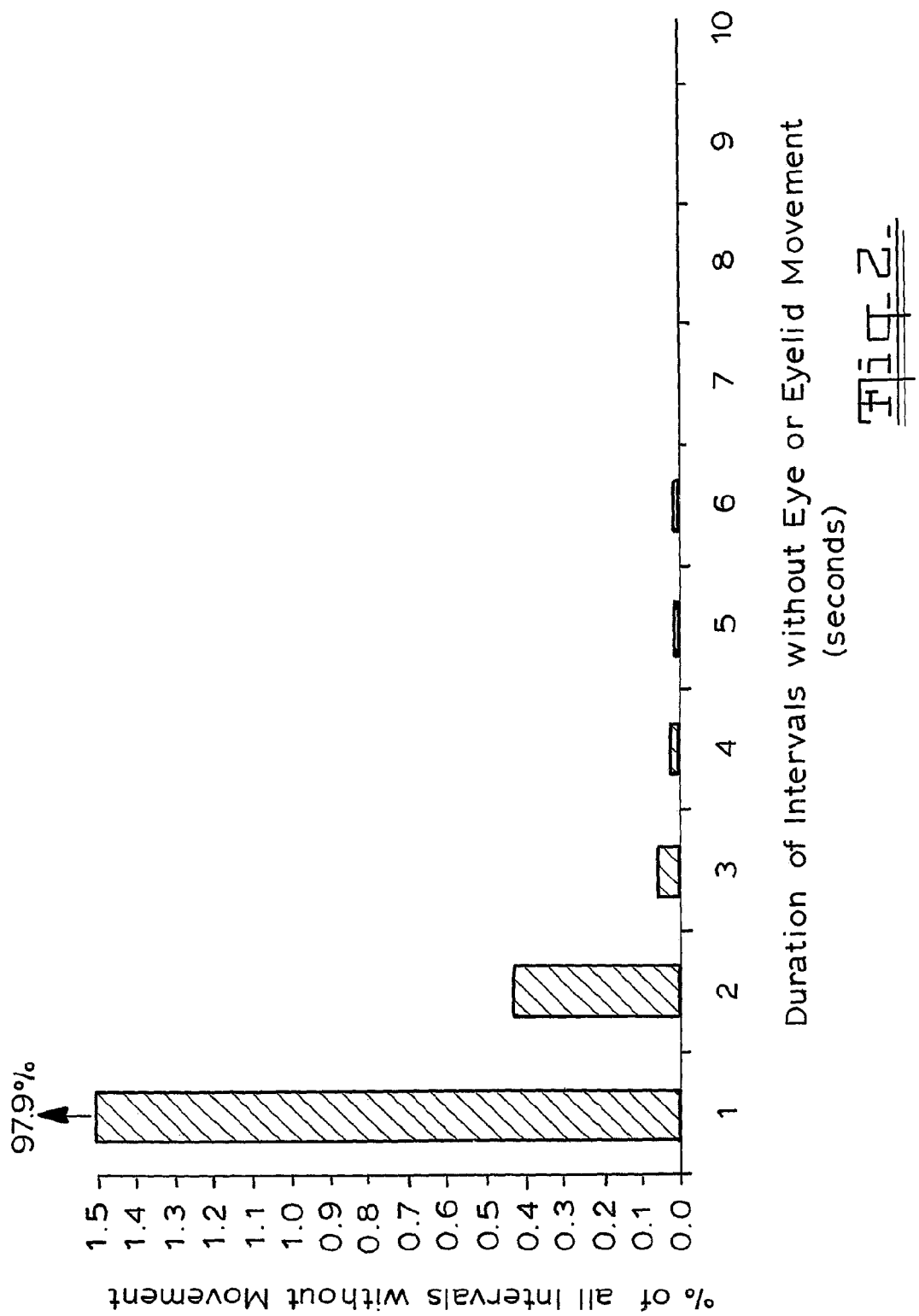
FIG. 2 is a frequency histogram illustrating the frequency of various periods of ocular quiescence in car drivers.

FIG. 1 is a frequency histogram of 59,310 intervals without eye or eyelid movement in two train drivers over 4 hours. FIG. 2 is a frequency histogram of 141278 intervals without eye or eyelid movement in seven car drivers over 6 hours. As can be seen from the survey results illustrated in FIGS. 1 and 2 an ocular quiescent period of 4 or 5 seconds or greater is sufficiently rare that a warning which requires a response from the operator would not be too frequent to be irritating or annoying. The appropriate time can be determined by conducting a preliminary survey of a sample of drivers or operators for each type of vehicle or machine.

Figure 3:
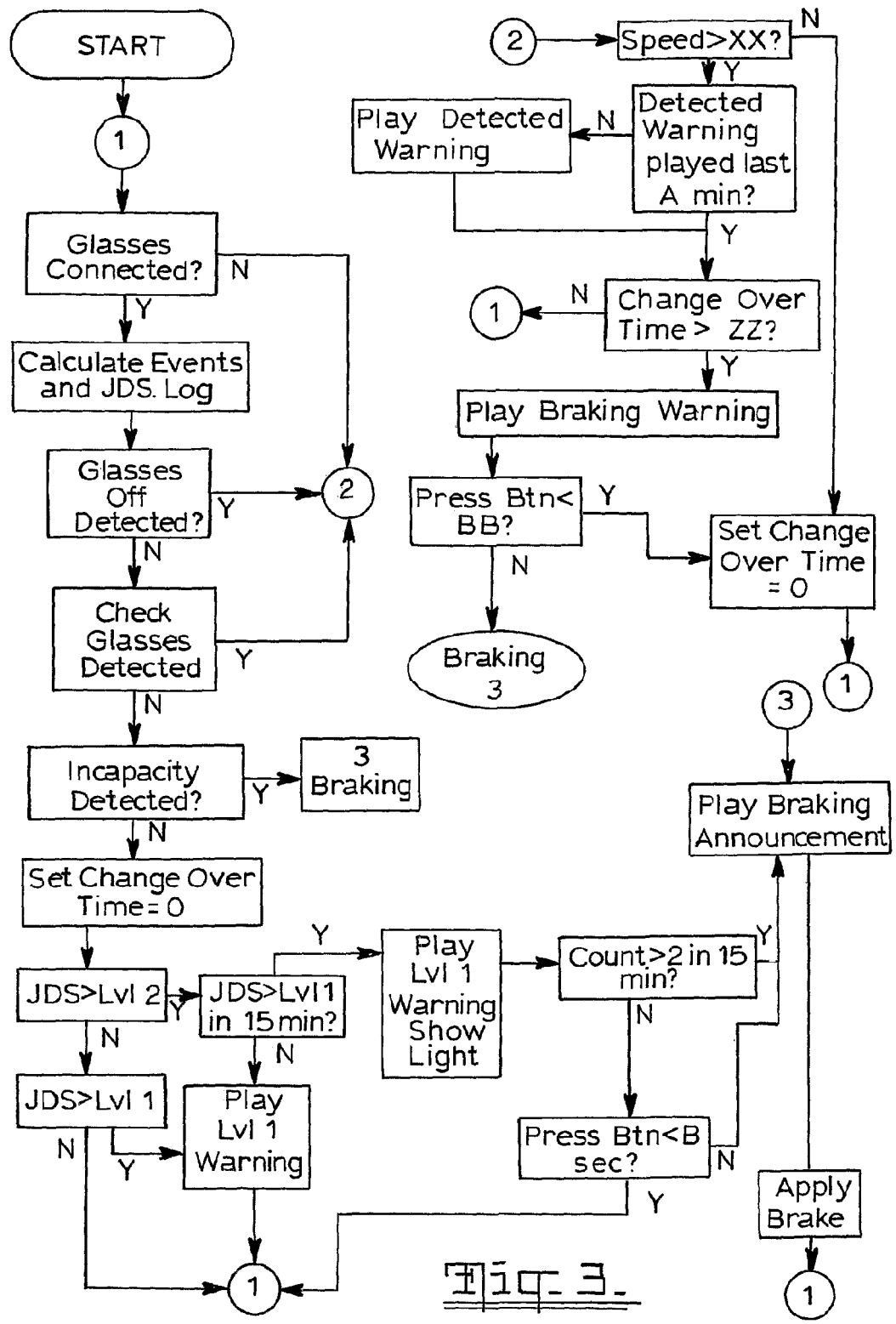
FIG. 3 is a flow chart of one embodiment of an incapacity monitor according to this invention.

FIG. 3 is a flow diagram of the operation of an incapacity monitor according to this invention designed for use on trains.

The first step in a cyclic procedure is to check if the glasses frame carrying the emitters and detectors is being worn. If they are not being worn and the speed of the train is above a preset minimum speed (such as in the shunting yard) a warning is given to prompt the train driver to put the glasses on. If no response is received the brake warning is given and then if no response is given the braking system of the train is automatically actuated.

When a period of ocular quiescence greater than the predetermined period is detected a warning is provided which requires the train driver to press a button and this response returns the detector to the normal detection cycle.

If no response is given within an appropriate predetermined period (about 2 seconds) the trains braking system is actuated.

If no period of ocular quiescence greater than the predetermined maximum is detected no warning is given.

The periods of ocular quiescence and the time required for a response can be determined by selecting values that will provide fewer warnings without increasing the risk of an accident.

From the above description it can be seen that the present invention provides a unique measure of incapacity and a reliable predictor of a person's capacity to operate machinery or vehicles.

Those skilled in the art will realize that the benefits of this invention can be achieved by embodiments of the apparatus and methodology other than those described without departing from the core teachings of this invention.

The invention claimed is:

1. A system for monitoring incapacity of a machine or vehicle operator which includes:
   a) spectacles to be worn by an operator incorporating at least an infra red emitter mounted on a lower spectacle frame and at least one infra red detector also mounted on the lower spectacle frame below one eye, to measure one or more of eye and eyelid movements including saccades and blinks in at least one eye of the operator;
   b) storage means to continuously record the measurements;
   c) a data processor to analyze said eye or eyelid movements to obtain a measure of the period of ocular quiescence of greater than 4 seconds;
   d) an alarm means triggered by said measurement reaching a predetermined value;
   e) an actuation means to respond to the alarm; and
   f) means to activate an emergency procedure if the alarm is not responded to within about 2 seconds.

2. An incapacity monitoring system as claimed in claim 1 for use in trains, in which the emergency procedure activates the vehicle braking system.

* * * * *